United States Patent
Kang

(10) Patent No.: US 10,139,378 B2
(45) Date of Patent: Nov. 27, 2018

(54) METHODS OF DETERMINING MOLECULAR WEIGHT AND COMONOMER CHARACTERISTICS OF A COPOLYMER IN POLYMER BLENDS

(71) Applicant: ExxonMobil Chemical Patents Inc., Baytown, TX (US)

(72) Inventor: Shuhui Kang, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 93 days.

(21) Appl. No.: 15/477,359

(22) Filed: Apr. 3, 2017

(65) Prior Publication Data

US 2017/0328873 A1    Nov. 16, 2017

Related U.S. Application Data

(60) Provisional application No. 62/336,961, filed on May 16, 2016.

(51) Int. Cl.

| | |
|---|---|
| *G06F 11/00* | (2006.01) |
| *G01N 30/86* | (2006.01) |
| *B01J 20/281* | (2006.01) |
| *G01N 30/74* | (2006.01) |
| *G01N 33/44* | (2006.01) |
| *G01N 30/00* | (2006.01) |
| *G01N 30/88* | (2006.01) |

(52) U.S. Cl.
CPC ............. *G01N 30/86* (2013.01); *G01N 30/48* (2013.01); *G01N 30/74* (2013.01); *G01N 30/8675* (2013.01); *G01N 33/442* (2013.01); *G01N 2030/486* (2013.01); *G01N 2030/885* (2013.01)

(58) Field of Classification Search
CPC ...................................................... G01N 30/86
See application file for complete search history.

(56) References Cited

U.S. PATENT DOCUMENTS

| 4,807,148 | A | * | 2/1989 | Lacey | ................ | G01N 30/8603 |
| | | | | | | 702/32 |
| 5,304,494 | A | * | 4/1994 | Eisenmann | ........ | G01N 33/2829 |
| | | | | | | 210/656 |

OTHER PUBLICATIONS

Kang et al., "A GPC-IR Analysis on Impact Copolymer Polypropylene (ICP)" in the International Symposium on GPC, Philadelphia (Oct. 20, 2015).

(Continued)

*Primary Examiner* — Phuong Huynh
(74) *Attorney, Agent, or Firm* — Kevin M. Faulkner

(57) ABSTRACT

A method for deconvoluting the molecular weight characteristics of the copolymer or rubber in an impact copolymer (ICP) comprising at least one copolymer or rubber and at least one homopolymer such as polypropylene, as well as a method of determining the comonomer characteristics of the rubber in an ICP, the methods comprising in part eluting a solubilized ICP through a gel permeation chromatographic (GPC) column to form an eluate comprising the rubber and/or polypropylene, measuring the Infrared (IR) absorption of at least the primary monomer-derived unit stretch frequency and the comonomer-derived unit in elution volume slices to determine the amount of comonomer, measuring the concentration of ICP using any detector, and determining the mass concentration, comonomer composition, and the total comonomer content of the ICP through the appropriate mathematical transformations.

25 Claims, 6 Drawing Sheets

(56) References Cited

OTHER PUBLICATIONS

Suarez, "Composition Effects on Ethylene/propylene Copolymers Studied by GPC-MALS and GPC-IR," European Polymer Journal, 2010, vol. 46, pp. 42-49.

Cheruthazhekatt et al., "Comprehensive High Temperature Two-dimensional Liquid Chromatography Combined with High Temperature Gradient Chromatography-infrared Spectroscopy for the Analysis of Impact Polypropylene Copolymers," Journal of Chromatography A, 2013, vol. 1286, pp. 69-82.

* cited by examiner

METHODS OF DETERMINING MOLECULAR WEIGHT AND COMONOMER CHARACTERISTICS OF A COPOLYMER IN POLYMER BLENDS

PRIORITY CLAIM

This application claims priority to and the benefit of U.S. Ser. No. 62/336,961, filed May 16, 2016 and is incorporated by reference in its entirety.

FIELD OF THE INVENTION

The present invention(s) relate in general to analytical chemical techniques for determining the molecular weight and comonomer characteristics of a copolymer in an intimate blend with another polymer.

BACKGROUND

One of the most common types of polymer blends is a blend of a homopolymer and copolymer, for example, a polyolefin homopolymer such as polypropylene and a polyolefin copolymer that consists only of olefin-derived units (ethylene, propylene, butene, etc.) or styrenic copolymers that include styrenic-derived units. Such blends are often called "impact copolymers" ("ICPs") in the industry, and for purposes of this disclosure can include any blend of two or more polyolefins, such as blends of $C_2$ to $C_8$ α-olefin homopolymers and copolymers, and especially blends of polypropylene and polyethylene and/or ethylene-propylene copolymers and/or ethylene-propylene elastomers.

Olefin-based impact copolymers are of particular use in the industry and can be made from a dual-reactor process in series, or by physical blending, and/or a dual catalyst process, where in either case one component such as a rubber phase is embedded or "dispersed" in another phase such as a homopolymer polypropylene ("PP") or "continuous" phase. The rubber can be any elastomeric copolymer ("EP"), but is preferably an ethylene-propylene copolymer. The rubber phase enhances the PP's toughness, a useful property for ICP materials. Information on its molecular weight ("MW", including number average, weight average, z-average, molecular weight distribution, etc.) and comonomer composition ("CC") provides an important guideline for catalyst screening, process optimization and product design. However, due to the similar MW range of the rubber and PP phases, the MWD (e.g., Mw/Mn) and CC of the polypropylene and rubber are typically convoluted with one another in conventional GPC or SEC (Gel Permeation Chromatography or Size Exclusion Chromatography) type of characterization. Thus, the MW characteristics of the rubber of ICPs cannot be directly studied without a thermal or chemical fractionation. Rubber phase separation or fractionation usually requires a lengthy and complicated procedure, and/or expensive tools.

Here, a method has been developed so that the MW characteristics of one phase of an ICP can be deconvoluted from the other phase using GPC-IR (GPC equipped with a multichannel IR detector). Another method is disclosed that allows characterization of the comonomer composition of rubber phase, together with the continuous phase or not, through a variable transformation of the GPC-IR data from MW space to CC space, which results in a quasi comonomer composition distribution (qCCD). This mathematical transformation reveals band-like features in qCCD that cannot be readily observed in the normal GPC data based on MW, therefore can be potentially used in polyolefin copolymer components analysis.

SUMMARY

Disclosed is a method of determining the molecular weight characteristics of the rubber in an impact copolymer (ICP) comprising at least one polyolefin copolymer (EP) and at least one polyolefin homopolymer (PP), where a blend of an ethylene-propylene copolymer or rubber with a polypropylene homopolymer is a particular example, the method comprising: eluting a solubilized ICP through a gel permeation chromatographic (GPC) column to form an eluate comprising the EP and/or PP; measuring the Infrared (IR) absorption of at least the primary monomer-derived unit stretch frequency and the comonomer-derived unit in elution volume slices (Ve) to determine the amount of comonomer ($S_{ICP}$), and measuring the concentration of ICP ($C_{ICP}$) using any detector; determining the mass concentration, comonomer composition at each Ve, and the total comonomer content ($Tc_2$) of the ICP; and for each Ve, calculating the amount of EP and PP using the following equations:

$$c_{EP}h_{EP}+c_{PP}h_{PP}=c_{ICP}h_{ICP}, \text{ and } c_{EP}h_{EP}s_{EP}+c_{PP}h_{PP}s_{PP}=c_{ICP}h_{ICP}s_{ICP}$$

wherein "c" is the concentration of ICP, EP and PP; "h" is the mass constant for EP, ICP, and PP; and "s" is the weight percent of comonomer for each of EP, ICP, and PP.

Also disclosed is method of determining the comonomer characteristics of the rubber in an impact copolymer (ICP) comprising at least one rubber (EP) and at least one polypropylene (PP), the method comprising: eluting a solubilized ICP through a gel permeation chromatographic (GPC) column to form an eluate comprising the EP and/or PP; measuring the Infrared (IR) absorption of at least the primary monomer-derived unit stretch frequency and the comonomer-derived unit in each Ve to determine the amount of comonomer ($S_{ICP}$), and measuring the concentration of ICP ($C_{ICP}$) using any detector; determining the mass concentration, comonomer composition, and the total comonomer content ($Tc_2$) of the ICP at each Ve; converting the weight percent of comonomer at each Ve into MW and weight percent comonomer content (C2%) by assuming the material is a reference polymer with a known set of M-H parameters (K'/a'); and applying a variable transformation from MW to C2% by treating the MW and C2% at each Ve as a probability density about log MW using the algorithm:

$$g(y) = \begin{cases} f(x(y))/y' & y' > 0 \\ -f(x(y))/y' & y' < 0 \\ \sum_{sec\, i} |f_i(x_i(y))/y_i'| & y' < \& > 0 \end{cases},$$

where "x" is the log MW and "y" is the C2% at each Ve, and the functions $f(x)$ and $g(y)$ are the probability density or distribution function about log MW and C2% respectively; and y' and $y_i'$ are the derivatives of y (C2%) as a function of x (log MW).

DETAILED DESCRIPTION

Figure 1A:
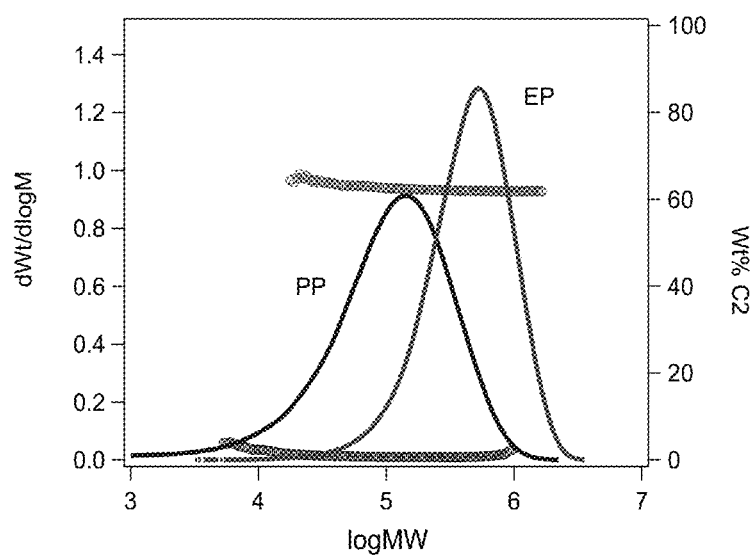
FIG. 1(a) is a plot of concentration as a function of MW and ethylene content (C2 or C2%) for a commercial PP and an EP samples.

The present inventions utilize the synergy between GPC and band-filter based IR5 detectors (e.g., PolymerChar™ GPC-IR) which provides a direct measurement of the CC of impact copolymers as a function of molecular weight with a great accuracy. Disclosed are new methods of ICP analysis with GPC-IR including the MWD deconvolution about the rubber portion of the ICP and the crystalline PP copolymer or homopolymer phase in ICP and the mathematical transformation from the MW space to CC space on GPC-IR chromatogram. The former can provide the MWD of each phase without depending on an expensive thermal or chemical fractionation procedure while the latter integrates the information from both MW and CC relationships in an ICP, providing a new look on the material structure from another facet.

As used herein, "polypropylene" refers to homopolymers of propylene-derived units and copolymers of propylene-derived units and within a range from 0.01 or 0.1 wt % to 5, or 10 wt %, by weight of the polymer, of ethylene and/or $C_4$ to $C_{10}$ α-olefin derived units.

As used herein, "rubber" and "copolymer" refers to polyolefin-based compositions that include within the range from 5, or 10, or 15 wt % to 50, or 55, or 60 wt % of at least one comonomer derived unit, preferably ethylene-derived units that are different from the remaining monomers, preferably propylene-derived units; also, "rubber" and "copolymer" can include polystyrene-based compositions that include at least one type of aromatic-based monomer unit. Preferably, "polyolefin-based" refers to compositions that consist of α-olefin derived units, excluding aromatic-based monomer units.

As used herein, "molecular weight characteristics" include the number average molecular weight (Mn), the weight average molecular weight (Mw), the z-average molecular weight (Mz), and ratios and combinations of these as is known in the art.

In industry, a combination of a series of tools such as FTIR, solid state NMR ("SSNMR") and Rheometer is often used to characterize ICP structure such as the total rubber content ($T_{EP}$), the commoner content in rubber phase, the overall commoner content (Wt % C2, or $T_{C2}$) and the melt flow characteristics. These methods are still relevant in the current inventions, but to further understand the detailed structure in each phase such as the MWD (Mw/Mn, or Mw/Mz, or Mz/Mn, etc.), the disclosed analytical methods are employed that eliminate the need for common fractionation procedures in which ICP samples are first dissolved in xylene at high T (>130° C.) and then precipitated at a lower temperature (usually room temperature). The soluble and the insoluble parts are collected and dried separately. Both soluble and insoluble fractions are then further tested with GPC.

GPC-IR can provide unique characterization of ICPs due to its quick turnaround time, high sensitivity, high reliability and high accuracy on both MW and CC characterization. Combining with some additional information and reasonable assumptions, the MW characteristics and comonomer characteristics for the rubber in a polymer blend such as an ICP can be deconvoluted mathematically.

Thus, in any embodiment is a method of determining the molecular weight characteristics of the rubber in an impact copolymer (ICP) comprising at least one rubber (EP) and at least one polypropylene (PP), the method comprising:

a) eluting a solubilized ICP through a gel permeation chromatographic (GPC) column to form an eluate comprising the EP and/or PP;

b) measuring the Infrared (IR) absorption of at least the primary monomer-derived unit stretch frequency and the comonomer-derived unit in elution volume slices (Ve) to determine the amount of comonomer ($S_{ICP}$), and measuring the concentration of ICP ($C_{ICP}$) using any detector;

c) determining the mass concentration, comonomer composition at each Ve, and the total comonomer content ($Tc_2$) of the ICP; and d) for each Ve, calculating the amount of EP and PP using the following equations (1) and (2):

$$c_{EP}h_{EP} + c_{PP}h_{PP} = c_{ICP}h_{ICP} \quad (1)$$

$$c_{EP}h_{EP}s_{EP} + c_{PP}h_{PP}s_{PP} = c_{ICP}h_{ICP}s_{ICP} \quad (2),$$

wherein "c" is the concentration of ICP, EP and PP; "h" is the mass constant for EP, ICP, and PP; and "s" is the weight percent of comonomer for each of EP, ICP, and PP; and wherein:

(i) when the total EP content ($T_{EP}$) is known, $S_{EP}$ is equal to the $Tc_2/T_{EP}$, and/or (ii) when the molecular weight characteristics of the PP is known, the value of $S_{EP}$ is chosen so that the $C_{PP}$ in each Ve has the same shape, and repeating the calculation until the $C_{PP}$ and the $C'_{PP}$ only differs by a multiplication factor.

In any embodiment described herein, the rubber is not physically separated from the polypropylene prior to elution. Further, it is desirable that the IR absorptions are recorded electronically and a computer is used to perform the calculations.

In any embodiment, for each Ve the molecular weight (MW) is calculated by using the following equation (3):

$$\log M_X = \frac{\log(K_{ST}/K_X)}{a_X+1} + \frac{a_{ST}+1}{a_X+1} \log M_{ST}, \quad (3)$$

where "ST" refers to a standard polymer used to calibrate the GPC, and the values of $a_{ST}$ and $K_{ST}$ are known, and wherein the "X" values are the EP or PP where "K" and "a" values are known for each of these.

In any embodiment, the values of K/a for PS are 0.000175/0.67, and wherein the "X" values are the EP or PP, and K/a values for PP are 0.000229/0.705 and for EP are calculated with the equations (4):

$$K = 0.000579(1 - 0.486 X_p - 0.069 X_p^2)/20000^{Trunc(10X_p)/1000},$$

$$a = 0.695 + Trunc(10X_p)/1000, \text{ and}$$

$$X_P = 1 - s_{EP}/100 \quad (4).$$

In any embodiment, for step (i) in the process described above, the total rubber content ($T_{EP}$) is known and the $S_{EP}$ is calculated with equation (5):

$$s_{EP} = Tc_2/T_{EP} \quad (5),$$

wherein the $T_{C2}$ is obtained by equation (6):

$$T_{C2} = \sum_i c_{ICP}^i s_{ICP}^i \Big/ \sum_i c_{ICP}^i. \quad (6)$$

In any embodiment, for step (ii) in the process described above, a concentration profile ($C'_{PP}$) for the PP portion of the ICP as a function of each Ve is obtained, and where a value of $S_{EP}$ is chosen and $C_{PP}$ calculated with equations (1) and the calculation is repeated until the $C_{PP}$ and the $C'_{PP}$ only differs by a multiplication factor.

In any embodiment, the PP and EP elute independently without interference with one another. Also in any embodiment, the $S_{EP}$ is constant across molecular weight of the EP.

In any embodiment, the rubber is an ethylene-propylene copolymer, and the Infrared (IR) measures the absorption of at least the $CH_2$ stretch frequency and the $CH_3$ stretch frequency in each Ve. Thus, desirably the rubber is an ethylene-propylene copolymer having within the range from 5, or 10, or 15 wt % to 50, or 55, or 60 wt % ethylene-derived units by weight of the rubber or copolymer. Also in any embodiment, the ICP has a rubber content within the range from 10, or 15, or 20 wt % to 40, or 45, or 50 wt % by weight of the ICP.

In any embodiment, the "h" value in equations (1) and (2) for the ICP, EP, and PP are each equivalent. This occurs in particular when only polyolefin-based impact copolymers are being studied. Thus in any embodiment where the polypropylene is a homopolymer, and $S_{PP}$ is zero, and wherein the "h" value for the ICP, EP, and PP are each equivalent, thus reducing the equations to equation (7):

$$c_{EP} = c_{ICP} s_{ICP}/s_{EP} \text{ and } c_{PP} = c_{ICP} - c_{EP} \quad (7),$$

Further, in any embodiment is a method of determining the molecular weight characteristics of the rubber in a polyolefin-based impact copolymer (ICP) comprising at least one rubber (EP) and at least one polypropylene (PP), the method comprising:

a) eluting a solubilized ICP through a gel permeation chromatographic (GPC) column to form an eluate comprising the EP and/or PP;

b) measuring the Infrared (IR) absorption of at least the primary monomer-derived unit stretch frequency and the comonomer-derived unit in each Ve to determine the amount of comonomer ($S_{ICP}$), and measuring the concentration of ICP ($C_{ICP}$) using any detector;

c) for each Ve, calculating the amount of EP and PP using the following equations (7):

$$c_{EP} = c_{ICP} s_{ICP}/s_{EP} \text{ and } c_{PP} = c_{ICP} - c_{EP} \quad (7),$$

wherein "c" is the concentration of EP, ICP, and PP; and "s" is the weight percent of comonomer for each of EP, ICP, and PP; and d) determining the concentration of EP and PP in each Ve, where:

(i) wherein the total rubber content ($T_{EP}$) is known and the $S_{EP}$ is calculated with equation (5):

$$s_{EP} = T_{C2}/T_{EP} \quad (5),$$

wherein the $T_{C2}$ is obtained by equation (6):

$$T_{C2} = \sum_i c_{ICP}^i s_{ICP}^i \Big/ \sum_i c_{ICP}^i, \quad (6)$$

or (ii) wherein the molecular weight characteristics of the PP is known, a concentration profile ($C'_{PP}$) for the PP portion of the ICP as a function of Ve is obtained, and wherein a value of $S_{EP}$ is chosen and $C_{PP}$ calculated with equations (7), repeating the calculation until the $C_{PP}$ and the $C'_{PP}$ only differs by a multiplication factor.

Also, in any embodiment is a method of determining the comonomer characteristics of the rubber in an impact copolymer (ICP) comprising at least one rubber (EP) and at least one polypropylene (PP), the method comprising:

a) eluting a solubilized ICP through a gel permeation chromatographic (GPC) column to form an eluate comprising the EP and/or PP;

b) measuring the Infrared (IR) absorption of at least the primary monomer-derived unit stretch frequency and the comonomer-derived unit in each Ve to determine the amount of comonomer ($S_{ICP}$), and measuring the concentration of ICP ($C_{ICP}$) using any detector;

c) determining the mass concentration, comonomer composition, and the total comonomer content ($Tc_2$) of the ICP at each Ve;

d) converting the weight percent of comonomer at each Ve into MW and weight percent comonomer content (C2%) by assuming the material is a reference polymer with a known set of M-H parameters (K'/a'); and e) applying a variable transformation from MW to C2% by treating the MW and C2% at each Ve as a probability density about log MW using the algorithm (8):

$$g(y) = \begin{cases} f(x(y))/y' & y' > 0 \\ -f(x(y))/y' & y' < 0 \\ \sum_{sec\, i} |f_i(x_i(y))/y_i'| & y' < \& > 0 \end{cases}, \quad (8)$$

where "x" is the log MW and "y" is the C2% at each Ve, and the functions $f(x)$ and $g(y)$ are the probability density or distribution function about log MW and C2% respectively; and y' and $y_i'$ are the derivatives of y (C2%) as a function of x (log MW).

In any embodiment, data smoothing is employed on any C2% as a function of log MW (y vs. x) trace to reduce data fluctuation caused by differential operation on discrete data points. This can be done by replacing C2% vs log MW curve with a smooth algebra function such as a high order polynomial function which is close enough to the raw data.

Also in any embodiment, sample pre-treatment is performed to remove shadowing effect of the polypropylene (or continuous) phase of the ICP. A proper sample treatment such as solvent extraction or thermal fractionation may be used in any embodiment to partially or completely remove the PP component so that the rubber phase is not overshadowed by PP phase.

In any embodiment is a chromatographic system comprising at least a GPC column, and having detectors in which the output is captured by a computing system comprising code to convert the output into a concentration as a function of molecular weight and/or comonomer composition by the methods described herein for at least the rubber component of the ICP. Such a computing system might also include means for sample pre-treatment and data smoothing. As used herein, a "computer" or "computing system" is a general purpose device that can be coded or programmed to carry out a set of arithmetic or logical operations automatically, and may also be capable of either manual data input or automatic acceptance of data from a source or output such as a chromatographic detector.

The various descriptive elements and numerical ranges disclosed herein for the inventive methods can be combined with other descriptive elements and numerical ranges to describe the invention(s); further, for a given element, any upper numerical limit can be combined with any lower numerical limit described herein, including the examples in jurisdictions that allow such combinations. The features of the inventions are demonstrated in the following non-limiting examples.

EXAMPLES

The molecular weight characteristics and the comonomer content (C2%, C3%, etc.) of the ICP and other polymers described herein were determined with a high temperature Gel Permeation Chromatography (PolymerChar GPC-IR) equipped with a multiple-channel band filter based Infrared detector ensemble IR5, in which a broad-band channel is used to measure the polymer concentration while two narrow-band channels are used for characterizing composition. Three Agilent PLgel 10 μm Mixed-B LS columns with total plate counts above 22000 were used to provide polymer separation. Aldrich reagent grade 1,2,4-trichlorobenzene (TCB) with 300 ppm antioxidant butylated hydroxytoluene (BHT) was used as the mobile phase. The TCB mixture is filtered through a 0.1 μm Teflon filter and degassed with an online degasser before entering the GPC instrument. The nominal flow rate is 1.0 mL/min and the nominal injection volume was 200 μL. The whole system including transfer lines, columns, and detectors were contained in an oven maintained at 145° C. An amount of polymer sample was weighed and sealed in a standard vial with 10 μL flow marker (heptane) added to it. After loading the vial in the autosampler, polymer was automatically dissolved in the instrument with 8 mL added TCB solvent. The polymer was dissolved at 160° C. with continuous shaking for about 2 hour for PP and ICP samples. The TCB densities used in concentration calculation are 1.463 g/ml at room temperature and 1.284 g/ml at 145° C. The sample solution concentration was from 0.2 to 2.0 mg/ml, with lower concentrations being used for higher molecular weight samples.

The concentration, c, at each point in the chromatogram was calculated from the baseline-subtracted IR5 broadband signal, I, using the following equation:

$$c = \alpha I$$

where $\alpha$ is the mass constant determined with PE or PP standards. The mass recovery was calculated from the ratio of the integrated area of the concentration chromatography over elution volume slices (Ve) and the injection mass which is equal to the pre-determined concentration multiplied by injection loop volume.

The molecular weight was determined by combining universal calibration relationship with the column calibration which is performed with a series of monodispersed polystyrene (PS) standards. The MW is calculated at each Ve with the following equation:

$$\log M_X = \frac{\log(K_{PS}/K_X)}{a_X + 1} + \frac{a_{PS} + 1}{a_X + 1} \log M_{PS}$$

where the variables with subscript "X" standing for the test sample while those with subscript "PS" standing for PS. In this method, $a_{PS}=0.67$ and $K_{PS}=0.000175$ while $a_x$ and $K_x$ are obtained from published literature. Specifically, a/K=0.695/0.000579 for PE and 0.705/0.000229 for PP.

The comonomer composition was determined by the ratio of the IR detector intensity corresponding to $CH_2$ and $CH_3$ channel calibrated with a series of PE and PP homo/copolymer standards whose nominal value are predetermined by NMR or FTIR. Unless measured by solid state $^{13}C$ NMR, the ethylene content of the polymers was measured using infrared spectroscopy following ASTM method D 3900-05a, "Standard Test Methods for Rubber-Determination of Ethylene Units in Ethylene-Propylene Copolymers (EPM) and in Ethylene-Propylene-Diene Terpolymers (EPDM) by Infrared Spectroscopy".

ICPs used in the deconvolution method study were either obtained from commercial sources or made in ExxonMobil commercial or pilot plants. ICPs used in qCCD study were synthesized in ExxonMobil lab reactors with the assistance of various solvents. The fractionation procedure of ICP samples was as follows: ICP samples are dissolved in p-xylene at 130° C. for 2 hours with agitation. The solution is then precipitated at 85° C. for 3 to 5 hrs followed by filtration. The soluble phase are further precipitated with non-solvent and then filtered and dried under $N_2$ protection overnight.

Molecular Weight Deconvolution

The ICPs in the examples were binary mixtures of an ethylene-propylene copolymer and PP homopolymer. Since the concentration and the CC were simultaneously measured in GPC-IR, a mathematical relationship between the two components can be expressed in the following two equations (1) and (2) at each Ve:

Equation 1: $c_{EP}h_{EP} + c_{PP}h_{PP} = c_{ICP}h_{ICP}$ (1)

Equation 2: $c_{EP}h_{EP}s_{EP} + c_{PP}h_{PP}s_{PP} = c_{ICP}h_{ICP}s_{ICP}$ (2), where the "c", "h" and "s" stand for the concentration, the mass constant and the Wt % C2 respectively. For an ICP system, $s_{PP} \approx 0$ and an approximate relationship exists among the mass constants: $h_{EP} \approx h_{PP} \approx h_{ICP}$. Therefore, only three variables ($c_{EP}$, $c_{PP}$, and $s_{EP}$) are left unknown. One more condition or equation is used to determine the "C" values. Two methods were developed and shown below.

Method A: Total Rubber ($T_{EP}$) is Known.

In the case where $T_{EP}$ was known, such as in the case where an ICP is obtained and analyzed by solid state NMR to determine the comonomer identity and content, the $s_{EP}$ can be calculated from the total comonomer content (ethylene in this case) ($T_{C2}$) if assuming it is a constant across the MW using equation (3):

Equation 3: $s_{EP} = Tc_2/T_{EP}$  (3).

The other two variables ($c_{EP}$, $c_{PP}$) thus can be resolved from equations (1) and (2).

Method B: the PP Sample is Available.

In the case where the homopolymer PP sample was available, such as an experimental grade of ICP being manufactured by the supplier, its MW characteristics were directly measured from GPC. Here the value for $s_{EP}$ can be so chosen such that the resultant PP MW characteristics were deconvoluted from the parent ICP sample such that it matches that for the pure PP phase.

It should be mentioned that Method B is not equivalent to the curve fitting method widely used in data analysis in polymer analysis. This is because, for instance, the MWD of PP or EP in a commercial product may not follow a regular shape that can be expressed with a simple mathematical function such as Gaussian, Lorentz, etc. In some situations, the MWD (Mw/Mn) can be bimodal or multi-modal. Method B is applicable for any distribution about the MW.

The above two methods provide a polymer concentration profile as a function of Ve. Next, a step to convert the concentration profile to MW or Ve to MW was performed. The conversion was done separately for PP and EP because polymer is eluted in GPC by hydrodynamic volume instead of MW. To obtain the MW characteristics of each component, it was assumed that polymer molecules elute independently without interfering with each other. Therefore the MW for both EP and PP can be calculated independently according to the universal calibration relationship and the Mark-Houwink (M-H) equation with polystyrene (PS) as the calibration standards as described above. The M-H parameters for EP depend on the $S_{EP}$ and were calculated with an empirical relationship (4):

$K = 0.000579(1 - 0.486 X_p - 0.069 X_p^2)/200,000^{Trunc(10X_p)/1000}$ $a = 0.695 + Trunc(10X_p)/1000$  (4), where the Xp is the weight percentage of propylene in EP (5):

$X_P = 1 - S_{EP}/100$  (5).

Figure 1B:
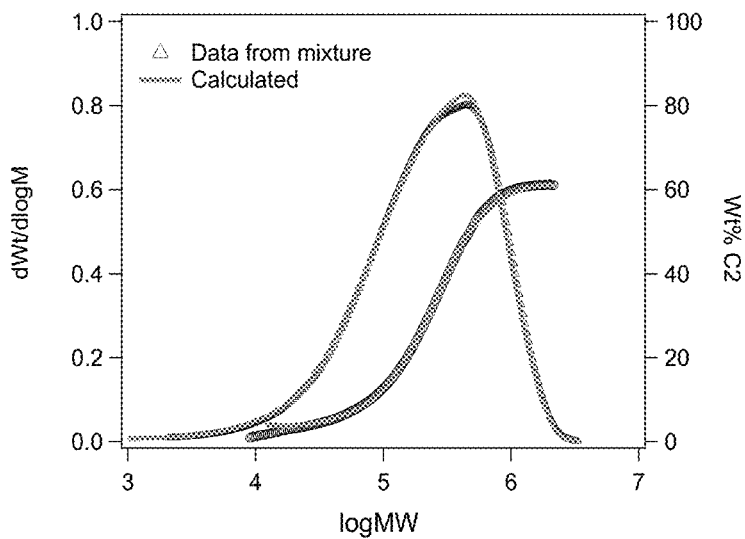
FIG. 1(b) is a comparison GPC plot between the measured MW and C2% content for a PP/EP mixture from FIG. 1(a) with mass ratio=48:52 and the calculated quantities by superposing the MWD and C2% from PP and EP with the given mass ratio. All the samples are analyzed as PP to facilitate the comparison (with same x-axis).

FIG. 1(a) shows the MW (corresponding to normalized concentration) and the CC (weight percent ethylene-derived units by weight of the polymer) GPC traces for a commercial PP homopolymer and experimental EP copolymer. FIG. 1(b) shows a comparison between the measured GPC traces of the blend of the PP and EP, and the calculated MWD and CC. It can be seen both MWD profile and the CC dependence between the measured and the calculated match very well with each other. The agreement demonstrates that the ideal elution assumption and the addition rule are valid in this GPC system. Since the solution for the equation (1) and (2) under the condition listed in Method A and B are unique, the result shown in FIG. 1(b) is also a validation for these methods.

The MW deconvolution methods developed were used in analyzing commercial samples, developmental samples, and non-Ziegler-Natta samples. The results are shown below.

Case I: Commercial ICP Samples

Figure 2A:
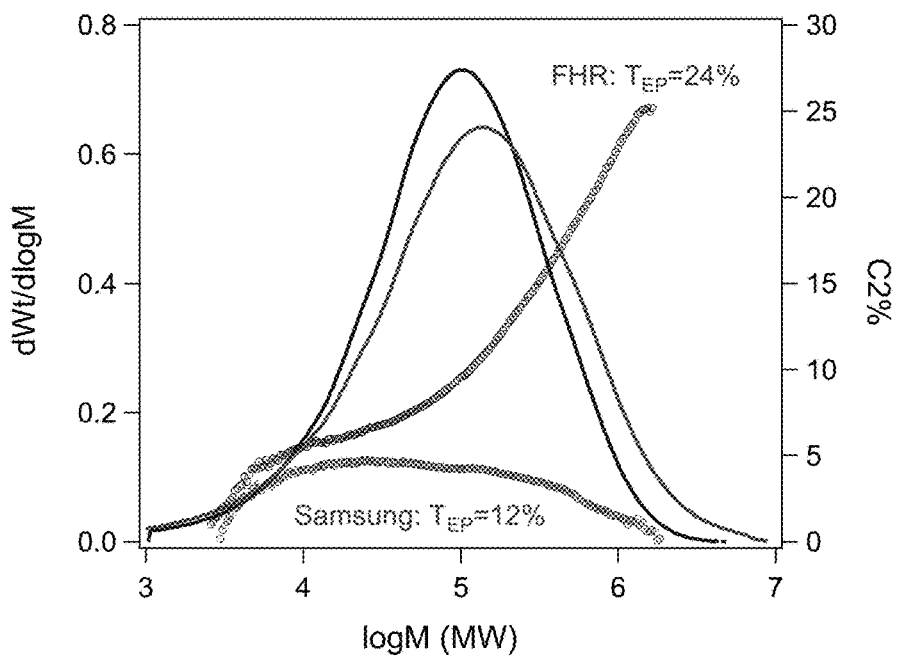
FIG. 2(a) is a plot of concentration as a function of MW and C2% plots measured with GPC-IR for two commercial ICPs.
Figure 2B:
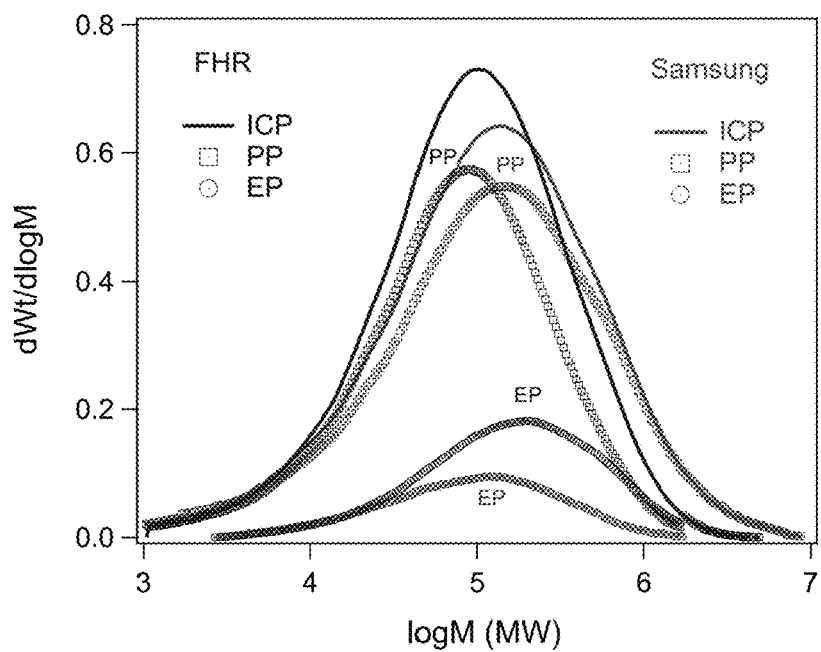
FIG. 2(b) is a plot of concentration as a function of MW and C2% plots of ICP is deconvoluted into two phases (PP and EP) based on Method A. The total amount of EP ($T_{EP}$) value shown in the figure is measured with solid state NMR.

FIG. 2(a) shows the MW GPC trace and C2% trace for two commercial ICPs for two different applications, while FIG. 2(b) is the deconvoluted MW traces for the PP and EP components. The FHR ICP is used for automotive while Samsung ICP is used for appliances. The MW trace for the Samsung ICP is shifted towards higher MW than the FHR ICP, while the inventive deconvolution using Method A demonstrates that its EP rubber has a MW that was actually lower than FHR's rubber phase. In addition, the deconvolution also reveals the MW difference between PP and EP phase inside the ICP. For the FHR sample, the MW of the EP component was higher than PP due to the requirement of high impact strength in automobile application; for the Samsung ICP, it was the opposite because impact strength is not the most demanded property for appliance application.

Case II: Developmental ICPs

Figure 3A:
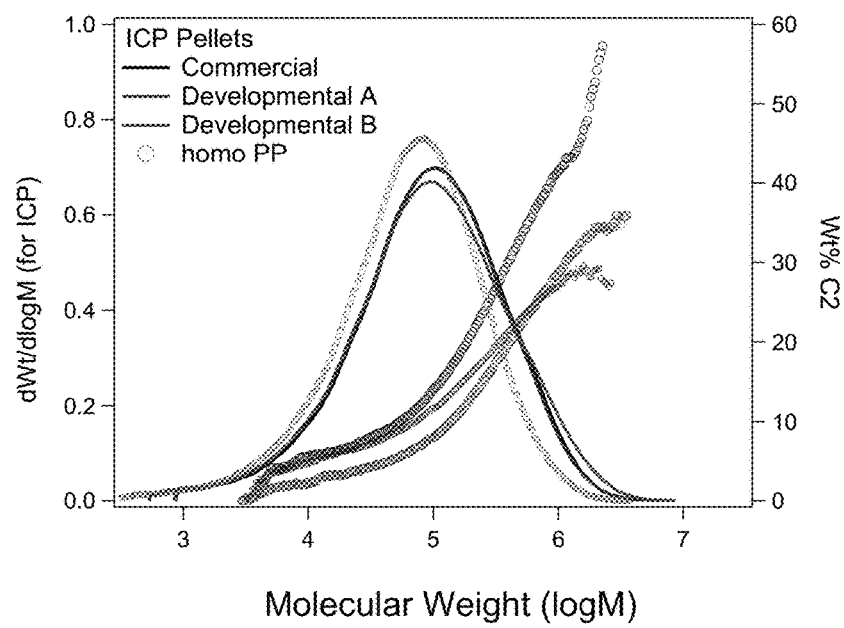
FIG. 3(a) is a plot of concentration as a function of MW and C2% plots for one commercial and two developmental ICPs together with the MW profile of PP homopolymer.
Figure 3B:
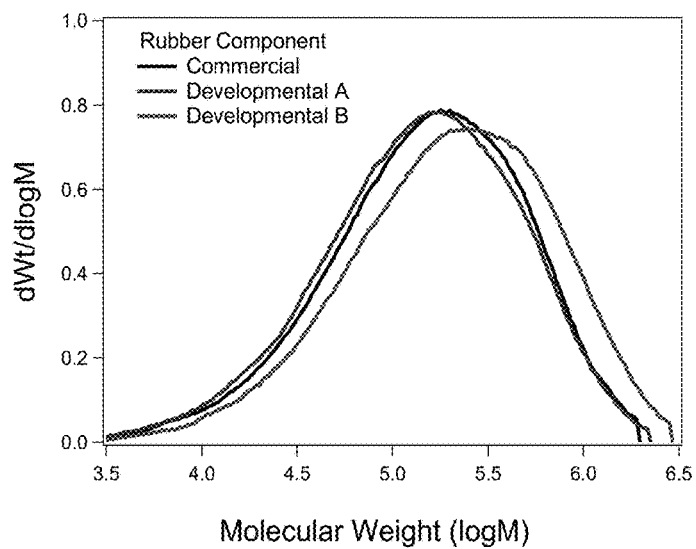
FIG. 3(b) is a deconvoluted plot of the MW profile of the rubber phase for the three ICPs in FIG. 3(a).

The PP phase is generally available for developmental ICPs and thus the $T_{EP}$ measurement is not needed because it can be calculated using Method B. FIG. 3(a) shows the MWD-C2% GPC traces for two developmental ICPs and one commercialized ICP together with the PP sample which is made under the same condition in all of these ICPs. The MWDs of rubber phase are deconvoluted for the three ICPs and plotted together in FIG. 3(b) for comparison. The cutoffs in the traces in FIG. 3(b) at the MWD tail are caused by missing CC values which are set to zero by the instrument software due to low detector sensitivity at low polymer concentration. A slight difference in the MWD and the relative rubber content can be observed among the EPs in them. The $T_{EP}$ values are found to be (30%, 29%, 25%) for the commercial, developmental A and developmental B respectively which is close to the numbers (26%, 28%, 25%) obtained with current test method (SS NMR+FTIR) as shown in Table 1. The consistency is also a validation for this method.

TABLE 1

Comparison between current method (SS NMR + FTIR) and the deconvolution method (GPC-IR) about the characterization of $T_{EP}/S_{EP}/T_{c2}$ for three ICPs

| Sample No. | $T_{EP}$ (SS-NMR/GPC) | $S_{EP}$ (SS-NMR/GPC) | $T_{c2}$ (SS-NMR/GPC) |
|---|---|---|---|
| Commercial | 26/30 | 58/55 | 15.1/16.5 |
| Developmental A | 28/29 | 42/43 | 11.5/12.3 |
| Developmental B | 25/25 | 40/42 | 10.0/10.4 |

Case III. ICP with Bimodal PP.

Figure 4:
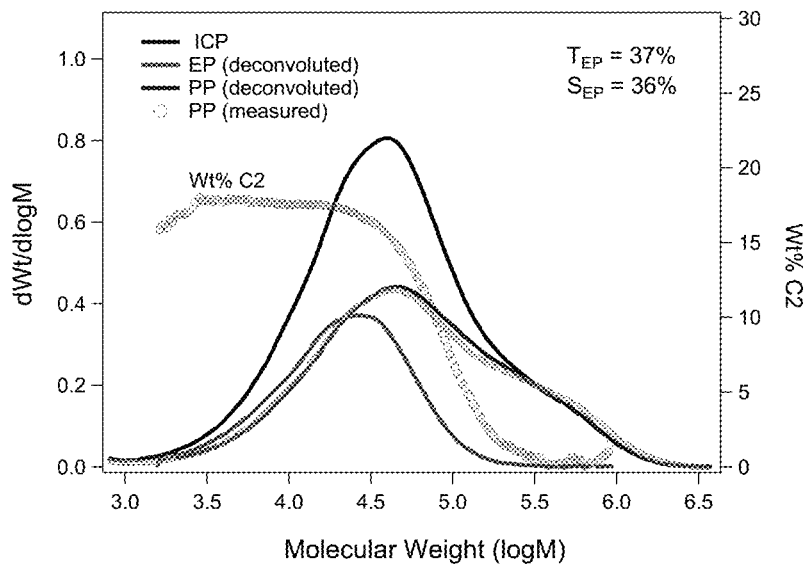
FIG. 4 is a plot C2% as a function of MW for a non-ZN ICP and the deconvoluted MWDs for PP and EP phases.

FIG. 4 shows MWD and C2% plots for a developmental ICP made from single site catalyst in which the PP phase is bimodal. The calculated MWD for rubber phase and PP phase are also shown in this figure together with the measured MWD of PP. The $T_{EP}$ and $S_{EP}$ are found to be 37% and 36% with Method B. This analysis quickly revealed that the new ICP has very high rubber content but low rubber MW, suggesting that further optimization is necessary.

Transforming from MW to CC Space

GPC-IR provides the MW and the comonomer composition dependence (CCD) on MW. By applying the present mathematical transformation from MW space to CC space, the data can be re-plotted as quasi-composition distribution (qCCD). The qCCD reveals a spectra-like feature so that a sample can be easily quantified or compared with other samples in terms of "band" position, intensity and width.

Mathematical transformation principle: MWD and qCCD are treated as a probability density about MW and CC respectively. They can be converted from one to another through a relationship between them, the CCD. The algorithm for probability density calculation is shown in the following equations (6):

$$g(y) = \begin{cases} f(x(y))/y' & y' > 0 \\ -f(x(y))/y' & y' < 0 \\ \sum_{sec\, i} |f_i(x_i(y))/y'_i| & y' < \& > 0 \end{cases} \quad (6)$$

where "x" is the log MW and "y" is the C2% at each Ve, and the functions $f(x)$ and $g(y)$ are the probability density or distribution function about log MW and C2% respectively. Three scenarios have to be considered: (1) the CC monotonically increases; (2) the CC monotonically decreases; (3) the CC sometimes increases, sometimes decrease.

Data smoothing: CCD includes discrete data points. To conduct a differential operation, it needs to be replaced by a smooth algebra function such as polynomial function which is close enough to the raw data.

Sample pre-treatment: The MW-CC space transformation can be directly applied on ICP samples. In most ICPs, the PP is the dominant phase and the EP phase is overshadowed by it. To better study the EP phase, a proper sample treatment such as solvent extraction or temperature fractionation is needed to partially or completely remove the PP component so that the convolution between PP and EP can be broken.

Case I: ICP Samples as a Whole

Figure 5A:
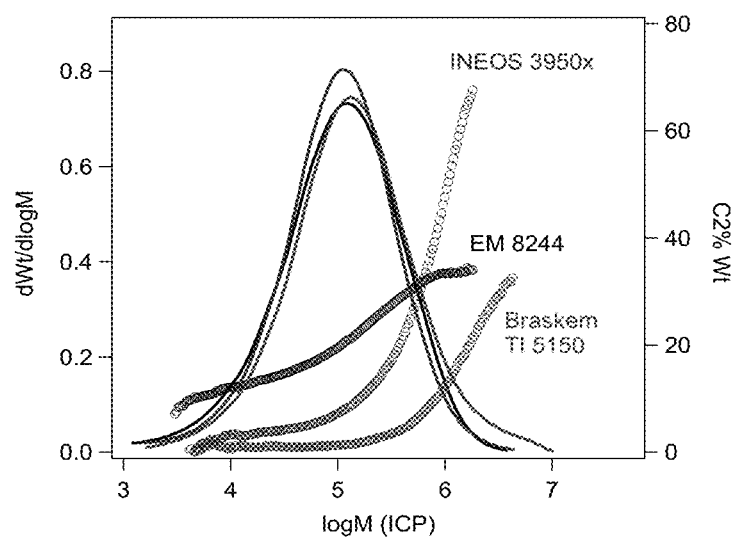
FIG. 5(a) is a plot of MW and CCD measured with GPC-IR.
Figure 5B:
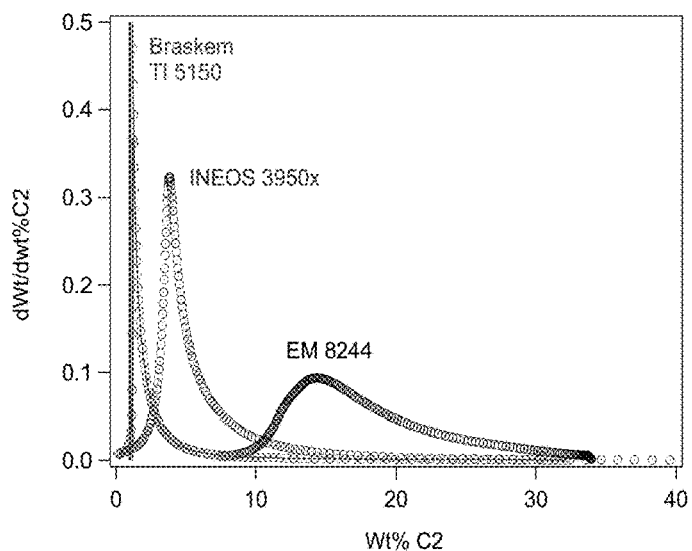
FIG. 5(b) is a plot of the qCCD transformed from FIG. 5(a).

Three commercial ICP samples were tested with GPC-IR and their MWDs were transformed into qCCDs which are shown in FIG. 5(a). FIG. 5(a) shows that the three samples have similar MWDs and the major differences exist in their CCDs. However these differences can be more significantly and quantitatively shown in their qCCDs in FIG. 5(b) figure. The qCCD seems to have integrated the features from both MWD and CCD in which the peak position indicates the majority CC in ICP while the peak width indicates the CC range. The significance in their qCCD differences can make them easily identified.

Case II: Fractionated ICP Soluble Phase

Figure 6A:
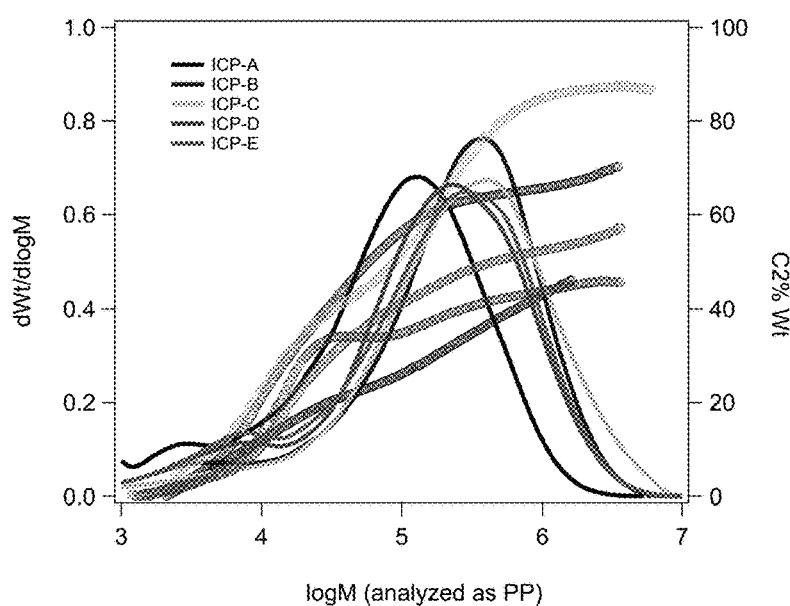
FIG. 6(a) is a plot of MW and CCD of ICP-solubles from five different ICP samples.
Figure 6B:
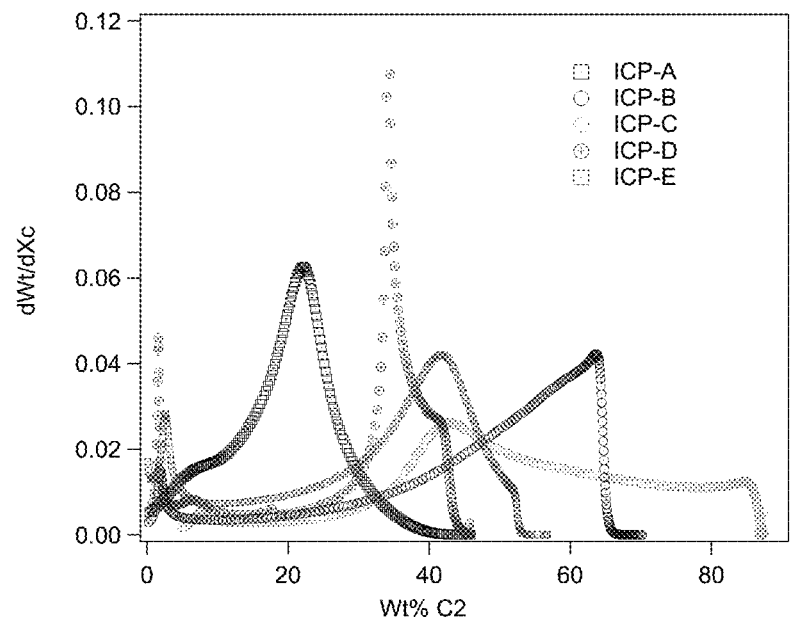
FIG. 6(b) is the corresponding qCCD for the same 5 ICP solubles in FIG. 6(a).

Five different ICP samples were fractionated with xylene solvent as described above. FIG. 6(a) shows their MWDs and CCDs. FIG. 6(b) shows the corresponding qCCDs after transformation. Each of these ICP's is made by solution phase using Ziegler-Natta catalysts, wherein the continuous phase in each is PP homopolymer, and the dispersed phase in each is an ethylene-propylene copolymer having within the range from 5 to 60 wt % ethylene-derived units. Although mathematical transformation does not increase or decrease the total amount of information, the visibility of some key information can be different. In MWD, all the polymer components are convoluted because there is only one major peak while in qCCD, these components are clearly revealed. FIG. 6(b) is more informative of comonomer composition and easy to compare because the band position, intensity and width could be related to certain structure of the samples. For example, all of the five samples show a common small peak around 0% C2, which can be easily identified as atactic PP, a component that is unwanted for ICP products. Other peaks are shown to be located in different positions with different shape across the five samples. Here we can use the "model ICP" (PP+EP mixture mentioned above) to provide some illustration.

Figure 7:
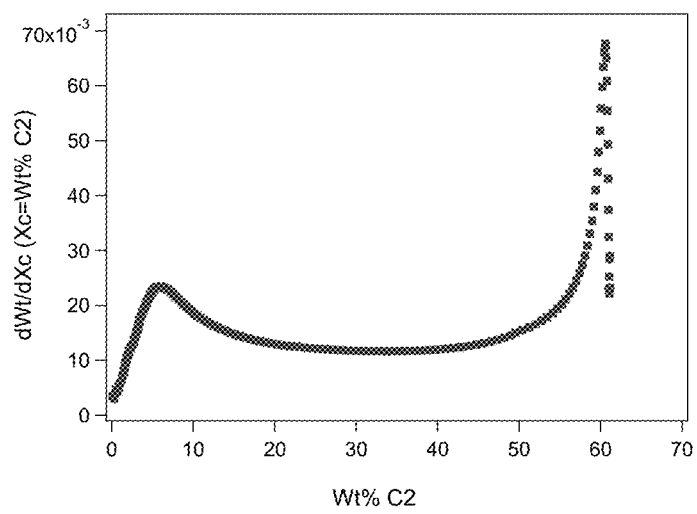
FIG. 7 is a qCCD transformed from the MW profile of the "model ICP" (PP+EP mixture) in FIG. 1(b) black lines where the two peaks (7% C2 and 60% C2) are corresponding to PP and EP components shown in FIG. 1(a).

FIG. 7 shows the qCCD plot transformed from MWD about the "model ICP" (FIG. 1(b) black lines). By comparing with FIG. 1(a), the GPC-IR chromatograms of the original samples, it can be seen that the two peaks (7% C2 and 60% C2) shown in FIG. 7 are indeed corresponding to PP and EP component. Due to MWD overlap, the peak position is shifted and the band is broadened. FIG. 7 demonstrates that qCCD could be qualitatively used to identify different EP components in an ICP sample.

For all jurisdictions in which the doctrine of "incorporation by reference" applies, all of the test methods, patent publications, patents and reference articles are hereby incorporated by reference either in their entirety or for the relevant portion for which they are referenced.

The invention claimed is:

1. A method of determining the molecular weight characteristics of the copolymer component in an impact copolymer (ICP) comprising at least one copolymer (EP) and at least one homopolymer (PP), the method comprising:
   a) eluting a solubilized ICP through a gel permeation chromatographic (GPC) column to form an eluate comprising the EP and/or PP;
   b) measuring the Infrared (IR) absorption of at least the primary monomer-derived unit stretch frequency and the comonomer-derived unit in elution volume slices (Ve) to determine the amount of comonomer ($S_{ICP}$), and measuring the concentration of ICP ($C_{ICP}$) using any detector;
   c) determining the mass concentration, comonomer composition at each Ve, and the total comonomer content ($Tc_2$) of the ICP; and
   d) for each Ve, calculating the amount of EP and PP using the following equations:

$$c_{EP}h_{EP} + c_{PP}h_{PP} = c_{ICP}h_{ICP}$$

$$c_{EP}h_{EP}s_{EP} + c_{PP}h_{PP}s_{PP} = c_{ICP}h_{ICP}s_{ICP},$$

wherein "c" is the concentration of ICP, EP and PP; "h" is the mass constant for EP, ICP, and PP; and "s" is the weight percent of comonomer for each of EP, ICP, and PP; and wherein:
   (i) when the total EP content ($T_{EP}$) is known, $S_{EP}$ is equal to the $Tc_2/T_{EP}$, and/or
   (ii) when the molecular weight characteristics of the PP is known, the value of $S_{EP}$ is chosen so that the $C_{PP}$ in each Ve has the same shape, and repeating the calculation until the $C_{PP}$ and the $C'_{PP}$ only differs by a multiplication factor.

2. The method of claim 1, wherein for each Ve the molecular weight (MW) is calculated by using the following equation:

$$\log M_X = \frac{\log(K_{ST}/K_X)}{a_X + 1} + \frac{a_{ST} + 1}{a_X + 1} \log M_{ST},$$

where "ST" refers to a standard polymer used to calibrate the GPC, and the values of $a_{ST}$ and $K_{ST}$ are known, and wherein the "X" values are the EP or PP where "K" and "a" values are known for each of these.

3. The method of claim 2, wherein the values of K/a for PS are 0.000175/0.67, and wherein the "X" values are the EP or PP, and K/a values for PP are 0.000229/0.705 and for EP are calculated with the equations:

$$K = 0.000579(1 - 0.486X_p - 0.069X_p^2)/20000^{Trunc(10X_p)/1000},$$

$a = 0.695 + Trunc(10X_p)/1000$, and $X_P = 1 - s_{EP}/100$.

4. The method of claim 1, wherein for step (i) the total rubber content ($T_{EP}$) is known and the $S_{EP}$ is calculated with equation:

$s_{EP} = Tc_2/T_{EP}$, wherein the $T_{C2}$ is obtained by equation:

$$T_{C2} = \sum_i c^i_{ICP} s^i_{ICP} / \sum_i c^i_{ICP}.$$

5. The method of claim 1, wherein for step (ii) a concentration profile ($C'_{PP}$) for the PP portion of the ICP as a function of each Ve is obtained, and where a value of $S_{EP}$ is chosen and $C_{PP}$ calculated with equations (1) and the calculation is repeated until the $C_{PP}$ and the $C'_{PP}$ only differs by a multiplication factor.

6. The method of claim 1, wherein the PP and EP elute independently without interference with one another.

7. The method of claim 1, wherein the $S_{EP}$ is constant across molecular weight of the EP.

8. The method of claim 1, wherein the rubber is not physically separated from the polypropylene prior to elution.

9. The method of claim 1, wherein the rubber is an ethylene-propylene copolymer having within the range from 5 wt % to 60 wt % ethylene-derived units by weight of the copolymer.

10. The method of claim 1, wherein the polypropylene is a homopolymer, and $S_{PP}$ is zero, and wherein the "h" value for the ICP, EP, and PP are each equivalent, thus reducing the equations to equation:

$c_{EP} = c_{ICP} s_{ICP}/s_{EP}$ and $c_{PP} = c_{ICP} - c_{EP}$.

11. The method of claim 1, wherein the ICP has a rubber content within the range from 10 wt % to 50 wt % by weight of the ICP.

12. A chromatographic system comprising at least a GPC column, and having detectors in which the output is captured by a computing system comprising code to convert the output into a concentration as a function of molecular weight by the method of claim 1 for at least the rubber component of the ICP.

13. A method of determining the molecular weight characteristics of the rubber in a polyolefin-based copolymer (ICP) comprising at least one rubber (EP) and at least one polypropylene (PP), the method comprising:
 a) eluting a solubilized ICP through a gel permeation chromatographic (GPC) column to form an eluate comprising the EP and/or PP;
 b) measuring the Infrared (IR) absorption of at least the primary monomer-derived unit stretch frequency and the comonomer-derived unit in each Ve to determine the amount of comonomer ($S_{ICP}$), and measuring the concentration of ICP ($C_{ICP}$) using any detector;
 c) for each Ve, calculating the amount of EP and PP using the following equations:

$c_{EP} = c_{ICP} s_{ICP}/s_{EP}$ and $c_{PP} = c_{ICP} - c_{EP}$, wherein "c" is the concentration of EP, ICP, and PP; and "s" is the weight percent of comonomer for each of EP, ICP, and PP; and d) determining the concentration of EP and PP in each Ve, where:
  (i) wherein the total rubber content ($T_{EP}$) is known and the $S_{EP}$ is calculated with equation:

$s_{EP} = Tc_2/T_{EP}$, wherein the $T_{C2}$ is obtained by equation:

$$T_{C2} = \sum_i c^i_{ICP} s^i_{ICP} / \sum_i c^i_{ICP},$$

or
  (ii) wherein the molecular weight characteristics of the PP is known, a concentration profile ($C'_{PP}$) for the PP portion of the ICP as a function of Ve is obtained, and wherein a value of $S_{EP}$ is chosen and $C_{PP}$ calculated with equations in step (c), repeating the calculation until the $C_{PP}$ and the $C'_{PP}$ only differs by a multiplication factor.

14. The method of claim 13, wherein for each Ve the molecular weight (MW) is calculated by using the following equation:

$$\log M_X = \frac{\log(K_{ST}/K_X)}{a_X + 1} + \frac{a_{ST} + 1}{a_X + 1} \log M_{ST},$$

where "ST" refers to a standard polymer used to calibrate the GPC, and the values of $a_{ST}$ and $K_{ST}$ are known, and wherein the "X" values are the EP or PP where "K" and "a" values are known for each of these.

15. The method of claim 14, wherein the values of K/a for PS are 0.000175/0.67, and wherein the "X" values are the EP or PP, and K/a values for PP are 0.000229/0.705 and for EP are calculated with the equations:

$$K = 0.000579(1 - 0.486X_p - 0.069X_p^2)/20000^{Trunc(10X_p)/1000},$$

$a = 0.695 + Trunc(10X_p)/1000$, and $X_P = 1 - s_{EP}/100$.

16. The method of claim 13, wherein the rubber is not physically separated from the polypropylene prior to elution.

17. The method of claim 13, wherein the rubber is an ethylene-propylene copolymer having within the range from 5 wt % to 60 wt % ethylene-derived units by weight of the copolymer.

18. The method of claim 13, wherein the ICP has a rubber content within the range from 10 wt % to 50 wt % by weight of the ICP.

19. The method of claim 13, wherein the IR absorptions are recorded electronically and a computer is used to perform the calculations.

20. A method of determining the comonomer characteristics of the rubber in an impact copolymer (ICP) comprising at least one rubber (EP) and at least one polypropylene (PP), the method comprising:
 a) eluting a solubilized ICP through a gel permeation chromatographic (GPC) column to form an eluate comprising the EP and/or PP;
 b) measuring the Infrared (IR) absorption of at least the primary monomer-derived unit stretch frequency and the comonomer-derived unit in each Ve to determine the amount of comonomer ($S_{ICP}$), and measuring the concentration of ICP ($C_{ICP}$) using any detector;

c) determining the mass concentration, comonomer composition, and the total comonomer content ($T_{C2}$) of the ICP at each Ve;

d) converting the weight percent of comonomer at each Ve into MW and weight percent comonomer content (C2%) by assuming the material is a reference polymer with a known set of M-H parameters (K'/a'); and e) applying a variable transformation from MW to C2% by treating the MW and C2% at each Ve as a probability density about log MW using the algorithm:

$$g(y) = \begin{cases} f(x(y))/y' & y' > 0 \\ -f(x(y))/y' & y' < 0 \\ \sum_{sec\, i} |f_i(x_i(y))/y_i'| & y' < \& > 0 \end{cases},$$

where "x" is the log MW and "y" is the C2% at each Ve, and the functions $f(x)$ and $g(y)$ are the probability density or distribution function about log MW and C2% respectively; and y' and $y_i$' are the derivatives of y (C2%) as a function of x (log MW).

21. The method of claim 20, wherein for each Ve the molecular weight (MW) is calculated by using the following equation:

$$\log M = \frac{\log(K_{ST}/K')}{a'+1} + \frac{a_{ST}+1}{a'+1} \log M_{ST},$$

where "ST" refers to a standard polymer used to calibrate the GPC, and the values of $a_{ST}$ and $K_{ST}$ are known, and wherein a' and K' are the values for the reference polymer.

22. The method of claim 20, wherein the values of $K_{ST}/a_{ST}$ for the standard polymer, polystyrene, are 0.000175/0.67, and wherein the K'/a' values for the reference polymer, polypropylene, are 0.000229/0.705.

23. The method of claim 20, wherein the rubber can be physically separated from the polypropylene prior to elution.

24. The method of claim 20, wherein the rubber is an ethylene-propylene copolymer having within the range from 5 wt % to 60 wt % ethylene-derived units by weight of the copolymer.

25. A chromatographic system comprising at least a GPC column, and having detectors in which the output is captured by a computing system comprising code to convert the output into a concentration as a function of comonomer content by the method of claim 20 for at least the rubber component of the ICP.

* * * * *